United States Patent [19]
Wentland et al.

[11] Patent Number: 5,532,263
[45] Date of Patent: Jul. 2, 1996

[54] BENZOTHIOPYRANOINDAZOLE ANTITUMOR AGENTS

[75] Inventors: Mark P. Wentland, Audubon; Robert B. Perni, Birdsboro, both of Pa.

[73] Assignee: Sterling Winthrop Inc., New York, N.Y.

[21] Appl. No.: 391,392

[22] Filed: Feb. 27, 1995

[51] Int. Cl.$^6$ .................. A61K 31/415; C07D 495/06
[52] U.S. Cl. .......................... 514/406; 548/358.5
[58] Field of Search ................ 548/358.5; 514/406

[56] References Cited

U.S. PATENT DOCUMENTS 3,505,341  4/1970  Elslager et al. .
3,963,740  6/1976  Elslager et al. .

FOREIGN PATENT DOCUMENTS 127389  12/1984  European Pat. Off. .
284966  10/1988  European Pat. Off. .

OTHER PUBLICATIONS

Blanz & French, J. Med. Chem., 1963, 6, 185–191.
Showalter et al, J. Med. Chem., 1988, 31, 1527–1538.
Bailly & Waring, Biochemistry, 1993, 32, 5985–5993.
Gordon & Chiang, The Journal of Pharmacology and Experimental Therapeutics, 1986, 236(1), 85–89.

*Primary Examiner*—Robert W. Ramsuer
*Attorney, Agent, or Firm*—Michael D. Alexander; Paul E. Dupont

[57]  ABSTRACT

Novel 2H-[1]benzothiopyrano[4,3,2-cd]indazoles are disclosed as antitumor agents. Compositions containing the benzothiopyranoindazoles and methods of treating tumors and cancer in mammals with benzothiopyranoindazoles are also disclosed.

13 Claims, No Drawings

BENZOTHIOPYRANOINDAZOLE ANTITUMOR AGENTS

FIELD OF THE INVENTION

The present invention relates to novel 2H-[1]benzothiopyrano [4,3, 2-cd]indazoles, to pharmaceutical compositions containing the benzothiopyranoindazoles, to methods of treating tumors with the benzothiopyranoindazoles and to methods of treating cancer in mammals with the compositions containing the benzothiopyranoindazoles.

INFORMATION DISCLOSURE STATEMENT

Elslager et al., European Patent Application No. 127,389, published Dec. 5, 1984, disclose N,N-diethyl-5-methyl-2H-[1]-benzothiopyrano[4,3,2-cd]indazole-2-ethanamine which is stated to be useful as an antitumor agent.

Beylin et al, European Patent Application No. 284,966, published Oct. 5, 1988, disclose a process for preparing compounds of the formula:

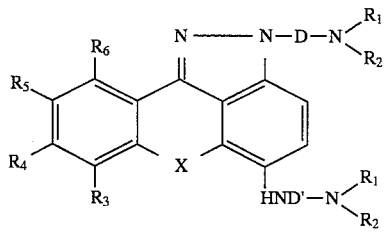

wherein X is oxygen, sulfur or selenium;

D and D' may be the same of different and are a straight or branched alkylene group of from two to five carbon atoms;

$R_1$ and $R_2$ may be the same or different and are hydrogen or an alkyl group of from two to eight carbon atoms which may be substituted by hydroxy;

$R_3$, $R_4$, $R_5$ and $R_5$ may be the same or different and are hydrogen or hydroxy; or a pharmaceutically acceptable salt thereof. The compounds are stated to possess antibacterial antifungal and antineoplastic activity. A similar disclosure is found in Beylin et al., J. Heterocyclic Chem., 1991, 28, 517–527.

Elslager et al., U.S. Pat. No. 3,505,341, issued Apr. 7, 1970, disclose compounds of the formula:

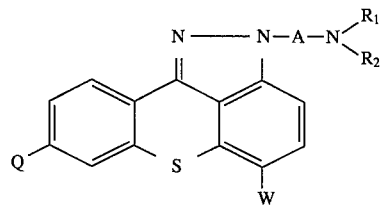

wherein

A is an alkylene radical containing 2 to 4 carbon atoms;

Q is a hydrogen or halogen atom;

$R_1$ and $R_2$ are the same or different and represent $C_1$–$C_4$ alkyl or together with the nitrogen atom [—$N(R_1)R_2$] a lower-alkylene radical containing 4 to 8 carbon atoms, 4 to 6 of which are joined in a ring with the nitrogen atom; and W is the aldehyde group —CHO or a methyl or hydroxymethyl group. The compounds are stated to possess antiparasitic and antibacterial activity.

Elslager, U.S. Pat. No. 3,963,740, issued Jun. 15, 1976, discloses compounds of the formula

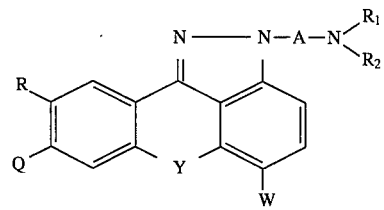

wherein

A is an alkylene radical containing 2 to 4 carbon atoms.

$R_1$ and $R_2$ are the same or different and represent $C_1$–$C_4$ alkyl or together a lower-alkylene radical containing 4 to 8 carbon atoms, 4 to 6 of which are joined in a ring with the nitrogen atom; and W is methyl, hydroxymethyl or acyloxymethyl wherein said acyl fragment contains from one to eight carbon atoms;

Y is S or O; and one of Q and R is hydrogen and the other is selected form hydrogen and a substituted halo or alkoxy group having from one to four carbon atoms. The compounds are stated to be intermediates in the preparation of the corresponding N-oxide derivative which are stated to be useful as parasiticidal agents. A similar disclosure is found in Elslager, U.S. Pat. No. 4,026,899, issued May 31, 1977.

Blanz and French, J. Med Chem., 1963, 6, 185–191, disclose 5-methyl- 2H-[1]benzothiopyrano[4,3, 2-cd]indazole (example 39) which was tested and found to be inactive as an antitumor agent.

Showalter et al., J. Med. Chem., 1988, 31, 1527–1538, disclose the synthesis and anticancer activity of a series of substituted 5-amino-2H-[1]benzothiopyrano[4,3,2-cd]indazoles. Specifically disclosed are N,N-diethyl-5-amino-2H-[1]benzothiopyrano[4,3,2-cd]indazole-2-ethanamine, N,N-diethyl-5-amino- 9-methoxy-2H-[1]benzothiopyrano[4,3,2-cd]indazole-2-ethanamine and N,N-diethyl-5-amino-9-hydroxy-2H-[1]benzothiopyrano[4,3,2-cd]indazole-2-ethanamine.

Bailly and Waring, Biochemistry 1993, 32, 5985–5993, disclose compounds of the formula:

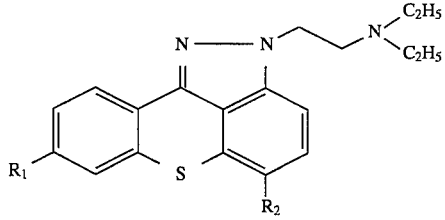

wherein $R_1$=$C_1$ and $R_2$=$CH_3$ ; $R_{1=Cl\ and\ R2}$=$CH_2OH$; $R_1$=H and $R_2$=$CH_3$; and $R_1$=H and $R_2$=$CH_2OH$. The compounds are stated to exhibit antitumor activity.

Gordon and Chiang, The Journal of Pharmacology and Experimental therapeutics 1986, 236(1), 85–89, disclose N,N-diethyl- 5-methyl-8-chloro-2H-[1]benzothiopyrano-[4,3,2-cd]indazole-2-ethanamine and N,N-diethyl-5-hydroxymethyl-8-chloro- 2H-[1]benzothiopyrano-[4,3,2-cd]indazole-2-ethanamine and their testing for antimuscarinic activity.

SUMMARY OF THE INVENTION

In a product aspect the invention relates to compounds of the formula I

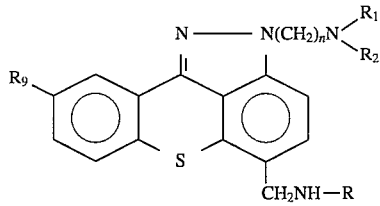

wherein n is 2 or 3;

R is hydrogen, lower-alkyl, C(O)H, C(O)$R_3$, $SO_2R_3$, and C(O)O$R_3$;

$R_1$ and $R_2$ are independently hydrogen or lower-alkyl;

$R_3$ is lower-alkyl; and $R_9$ is hydrogen, lower-alkyl, lower-alkoxy, or hydroxy; or a pharmaceutically acceptable acid-addition salt or solvate thereof. The compounds are useful for the treatment of tumors and cancers in mammals.

Lower-alkyl as used herein describes linear, branched or cyclic hydrocarbons containing four or fewer carbon atoms.

The term lower-alkoxy means linear or branched alkyloxy substituents having from one to about four carbon atoms, for example, methoxy, ethoxy, propoxy, isopropoxy, butoxy, sec-butoxy, and the like.

In a further product aspect the invention relates to compositions for treating tumors and cancer in mammals which comprise compounds of formula I together with pharmaceutically acceptable excipients or diluents.

In a process aspect the invention relates to a method for treating tumors in mammals which comprises administering to the mammal a compound of formula I.

In a further process aspect the invention relates to a method for treating cancer in a mammal which comprises administering to the mammal a composition of a compound of formula I together with pharmaceutically acceptable excipients or diluents.

DETAILED DESCRIPTION INCLUSIVE OF PREFERRED EMBODIMENTS

Preferred compounds of the invention are where n is 2 and $R_1$ and $R_2$ are each ethyl.

Even more preferred compounds of the invention are where R is $SO_2R_3$ and C(O)O$R_3$, and $R_3$ is methyl.

The most preferred compounds of the invention are where $R_9$ is hydroxy.

The synthesis of compounds of the invention may be outlined as shown in Schemes A.

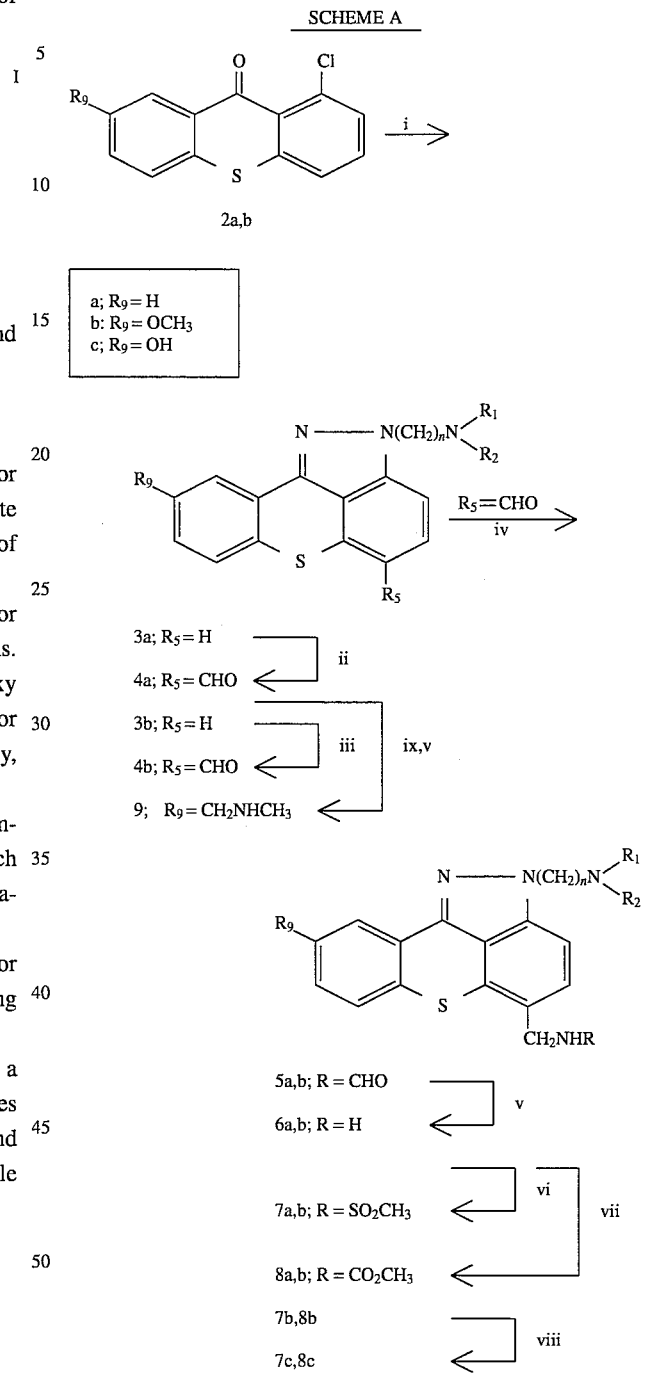

Reagents:
(i)

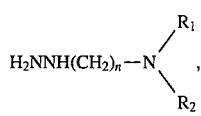

pyr, 115° C.

(ii) CHCl$_2$OCH$_3$, AlCl$_3$, CH$_2$Cl$_2$, 25° C.

(iii) POCl$_3$, DMF, 100° C.

(iv) HCONH$_2$, HCO$_2$H, 140° C.

(v) NaOH, MeOH, H$_2$O, 70° C.

(vi) CH$_3$SO$_2$Cl, pyr, CH$_2$Cl$_2$, 25° C.

(vii) CH$_3$OCOCl, Et$_3$N, CH$_2$Cl$_2$, 25° C.

(viii) BBr$_3$, CH$_2$Cl$_2$, −78° C.

(ix) HCONHCH$_3$, HCOOH, 140° C.

Treatment of thioxanthones 2a and 2b (each as a mixture with their corresponding 3-chloro regioisomer) with dialkylamino(alkyl)hydrazine in refluxing pyridine provides the core heterocyclic systems 3a and 3b, respectively. Compound 3a is treated with CHCl$_2$OCH$_3$/AlCl$_3$ to give the 5-formyl derivative 4a, while 3b is subjected to Vilsmeier conditions to give 4b. Treatment of 4a and 4b with formamide/formic acid (Leuckart conditions) provides 5a and 5b, respectively; these formamides are hydrolyzed to the corresponding amines 6a and 6b using aqueous methanolic NaOH. Using standard methodology, 6a and 6b are converted to the corresponding methansulfonamido and urethane derivatives 7a, 7b, 8a and 8b. The phenolic analogues 7c and 8c are made by treating 7b and 8b, respectively, with BBr$_3$/CH$_2$Cl$_2$ at −78° C. Compound 9 is made by treating 4a with HCONHCH$_3$/HCO$_2$H followed by base hydrolysis.

Simple chemical transformations which are conventional and well known to those skilled in the art of chemistry can be used for effecting changes in the functional groups of the compounds of the invention.

The compounds of formula I are useful both in the free base form and in the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. In practicing the present invention it is convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention are established by the mode of synthesis. Proton NMR spectra, obtained on a GE QE 300 NMR and chemical ionization mass spectra, obtained on a Nermag R 10—10 C are consistent with the assigned structures. Proton NMR multiplicity data are denoted by s (singlet), d (doublet), t (triplet), q (quartet), and m (multiplet). Coupling constants are reported in hertz. Combustion analyses (C,H,N) are performed by Quantitative Technologies, Inc. Whitehouse, N.J. and are within 0.4% of theoretical values. Reactions are performed under an N$_2$ atmosphere. The melting points are determined on Mel-Temp melting point apparatus in open capillaries, are given in degrees C. and are uncorrected. The starting materials are either commercially available or may be prepared by procedures well known in the art.

EXAMPLE 1

N,N-Diethyl-2H-[1]benzothiopyrano[4,3,2-cd]indazole-2-ethanamine

A solution of a 1:1 mixture of 1-chloro and 3-chlorothioxanthen-9-one (6.20 g, 25.2 mmol), N,N-diethyl-2-hydrazinoethanamine (4.20 g, 32.0 mmol) pyridine (50 mL) is heated at reflux for 24 hours and the solvent is removed in vacuo. The residue is dissolved in CHCl$_3$ and washed with water (3x). The organic layer is dried over Na$_2$SO$_4$ and concentrated in vacuo. The residue is flushed through a pad of silica gel eluting with EtOAc/hexane (10% to 40%), to give 2.42 g of the compound (30%). Recrystallization from hexanes gives the analytical sample, mp: 49°–50.5° C. $^1$H NMR (CDCl$_3$) 1.00 (6H; t), 2.56 (4H; q), 2.90 (2H; t), 4.30 (2H; t), 6.64 (1H; d), 6.84 (1H; d), 7.10–7.22 (4H; m), 8.02 (1H; dd) ppm. MS m/z 324 (MH$^+$). Anal. (C$_{19}$H$_{21}$N$_3$S) C, H, N.

EXAMPLE 2

N,N-Diethyl-9-methoxy-2H-[1]benzothiopyrano[4,3,2-cd]indazole-2-ethanamine

The compound is prepared and purified via the same procedure as shown in Example 1 from a 1:1 mixture of 1-chloro and 3-chloro-7-methoxythioxanthen-9-one in 39% yield as a yellow oil. $^1$H NMR (CDCl$_3$) 0.98 (6H; t), 2.56 (4H; q), 2.90 (2H; t), 3.82 (3H; s), 4.30 (2H; t), 6.62 (1H; d), 6.76 (1H; dd), 6.80 (1H; d), 7.08 (2H; two d's), 7.58 (1H; d) ppm. MS m/z 354 (MH$^+$). Anal. (C$_{20}$H$_{23}$N$_3$OS) C, H, N.

EXAMPLE 3

2-[2-(Diethylamino)ethyl]-2H-[1]benzothiopyrano-[4,3,2-cd]indazole-5-carboxaldehyde A suspension of aluminum chloride (1.76 g, 12.8 mmol) in CH$_2$Cl$_2$ (25 mL) is stirred at room temperature for 15 min and the compound of Example 1 (2.07 g, 6.38 mmol) in CH$_2$Cl$_2$ (15 mL) is added at 5° C. and the resulting mixture is stirred 10 min and cooled to 0° C. A solution of dichloromethyl methyl ether (1.52 g, 17.4 mmol) in 10 mL of CH$_2$Cl$_2$ is added dropwise over a period of 15 min. The mixture is allowed to warm to ambient temperature, stirred overnight and then diluted with of 2N HCl (10 mL) and cool water (100 mL). The mixture is poured into CHCl$_3$ (100 mL), basified with 2N NaOH solution to pH 8–9 and the layers are separated. The aqueous layer is extracted with CHCl$_3$ (40 mL). The combined organic layers are washed with water and dried over Na$_2$SO$_4$. Concentration and drying in vacuo gives crude aldehyde (2.16 g, 96%) which can be used without additional purification. The analytical sample is obtained by silica gel chromatography (EtOAc) following by recrystallization from EtOAc/hexane (1:2), mp: 81°–82.5° C. $^1$H NMR (CDCl$_3$) 0.95 (6H; t), 2.54 (4H; q), 2.95 (2H; t), 4.40 (2H; t), 7.02 (1H; d), 7.23–7.40 (2H; m), 7.51–7.54 (1H; m), 7.64 (1H; d), 8.17–8.20 (1H; m), 10.02 (1H; s)ppm. MS m/z 352 (MH$^+$). Anal. (C$_{20}$H$_{21}$N$_3$OS) C, H, N.

EXAMPLE 4

2-(2-(Diethylamino)ethyl)-9-methoxy-2H-[1]benzothiopyrano[4,3,2-cd]-indazole-5-carboxaldehyde To a stirred solution of the compound of Example 2 (1.60 g, 4.19 mmol) in dimethylformamide (45 mL) at room temperature is added dropwise, a solution of phosphorus oxychloride (1.6 mL) in DMF (5 mL). The reaction mixture is heated at 95°–100° C. for 18 h. Heat is removed and ice (50 g) is added. The mixture is stirred for 10 minutes and basified with 2N NaOH solution to pH 8–9. The basic solution is extracted with CHCl$_3$ and the extracts are washed with water three times, dried over Na$_2$SO$_4$, filtered, and concentrated in vacuo. The residue is purified by flash chromatography (hexane, hexane:EtOAc (60:40) and EtOAc (100%) to give the desired product (1.06 g, 61%) as a yellow oil. $^1$H NMR (CDCl$_3$) 0.98 (6H; t), 2.56 (4H; q), 2.96 (2H; t), 3.94 (3H; s), 4.42 (2H; t), 6.96–7.06 (2H; m), 7.48 (1H; d), 7.62–7.72 (2H; dd), 10.04 (1H; s) ppm.

EXAMPLE 5

N-[[2-[(2-(Diethylamino)ethyl]-2H-[1]benzothiopyrano[4,3,2-cd]indazol-5-yl]methyl]formamide A solution of the compound of Example 3 (1.64 g, 4.67 mmol) formic acid (1.8 g, 39 mmol) and formamide (30 mL), is heated to 140°–150° C. for 5 hours. The reaction mixture is poured into 40 mL of ice-water and basified with 2N NaOH solution to pH 8–9. The basic aqueous solution is extracted with CHCl$_3$. The organic layer is washed with water, dried and concentrated to give the crude product. The pure formamide is obtained by silica chromatography, eluting with 0.5% isopropylamine in EtOAc to afford the pure compound. (1.20 g, 67%), mp: 159.5°–161° C. $^1$H NMR (CDCl$_3$) 0.95 (6H; t), 2.56 (4H; q), 2.92 (2H; t), 4.36 (2H; t), 4.08 (2H; d), 6.83 (1H; d), 7.15 (1H; d), 7.18–7.30 (3H; m), 8.07–8.10 (1H; m), 8.26 (1H; s)ppm. MS m/z 381 (MH$^+$). Anal. (C$_{21}$H$_{24}$N$_4$OS) C, H, N.

EXAMPLE 6

N-[[2-[(2-(Diethylamino)ethyl]-9-methoxy-2H-[1]-benzothiopyrano[4,3,2-cd]indazol-5-yl]methyl]-formamide This compound is prepared in quantitiative yield via the same procedure used to synthesize the compound of Example 5 which could be used without additional purification: mp 125°–131° C. $^1$H NMR (CDCl$_3$) 0.92 (6H; t), 2.48 (4H; q), 2.82 (2H; t), 3.80 (3H; s), 4.22 (2H; t), 4.28 (2H; d), 6.70–6.80 (2H; m), 7.00–7.08 (2H; m), 7.42 (1H; d,) 8.08 (1H; s)ppm. MS m/z 412 (MH$^+$) . Anal. (C$_{22}$H$_{26}$N$_4$O$_2$.¼H$_2$O.

EXAMPLE 7

N-[[2-[(2-(Diethylamino)ethyl]-2H-[1]-benzothiopyrano[4,3,2-cd]indazol-5-yl]methyl]-N'-methylformamide This compound is prepared in 80% yield via the same procedure used to synthesize the compound of Example 5 except N-methyl formamide is used instead of formamide. The crude product is purified by silica gel chromatography (EtOAc/hexanes 1: 1) $^1$H NMR (CDCl$_3$) (two isomers, 2:3) 0.92 (6H; t), 2.50 (4H; q), 2.70–2.80 (3H; 2 s+s), 2.88 (2H; t), 4.2–4.36 (3.2H; m), 4.42 (0.8H; s), 6.80–7.30 (5H; m), 8.00 (1H; m), 8.10 (0.4H; s), 8.30 (0.6H; s) ppm.

EXAMPLE 8

2-[(2-(Diethylamino)ethyl]-2H-[1]-benzothiopyrano-[4,3,2-cd]indazole-5-methanamine To a solution containing the compound of Example 5 (2.76 g, 7.25mmol) in MeOH (100 mL) is added 10% NaOH solution.(50 mL) The mixture is heated at reflux for 5 hours. The reaction mixture is cooled down to room temperature and extracted with CHCl$_3$. The organic layers are washed with water and dried over Na$_2$SO$_4$. Concentration in vacuo gives the crude product. Purification by chromatography, with 2% Et$_3^N$ and 98% CHCl$_3$ affords the pure material as a viscous oil, 1.78 g (62%). Recrystallization from MeOH/EtOAc (2:10) gives the analytical sample, mp: 197°–199.5° C. '$H$ NMR (CDCl$_3$) 0.99 (6H; t), 2,54 (6H; q, s), 2.93 (2H; t), 3.79 (2H; s), 4.34 (2H; t), 6.87 (1H; d), 7.10–7.30 (4H; m), 8.01 (1H; m)ppm. MS m/z 353 (MH$^+$). Anal. (C$_{20}$H$_{24}$N$_4$S.HCl.½H$_2$O) C, H, N.

EXAMPLE 9

2-[(2-(Diethylamino)ethy]-9-methoxy-2H-[1]-benzothiopyrano[4,3,2-cd]indazole-5-methanamine The compound is prepared via the same procedure used to synthesize the compound of Example 8. Pure material is obtained by flash chromatography [hexane:EtOAc (50:50), EtOAc, CH$_2$Cl$_2$, 0.5–1% IPA in CH$_2$Cl$_2$] in 90% yield: mp 74°–76° C. $^1$H NMR (CDCl$_3$) 0.96 (6H; t), 2.52 (4H; q), 2.88 (2H; t), 3.72 (2H; s), 3.82 (3H; s), 4.28 (2H; t), 6.70–6.80 (2H; m), 7.10 (1H; d), 7.62 (1H; d)ppm. MS m/z 383 (MH$^+$). Anal (C$_{21}$H$_{26}$N$_4$OS) C, H, N.

EXAMPLE 10

N-methyl-2-[(2-(Diethylamino)ethyl]-2H-[1]-benzothiopyrano[4,3,2-cd]indazole-5-methanamine dihydrochloride hydrate This compound is prepared in 84% yield via the same procedure used to synthesize the compound of Example 8. The crude product is purified by silica gel chromatography (1% Et$_3$N: 0.5% MeOH: CHCl$_3$). The hydrochloride salt is prepared from 2N HCl solution, mp: 189°–193° C. $^1$H NMR (free base in CDCl$_3$) 0.96 (6H; t), 2,42 (3H; s), 2.53 (4H; q), 2.89 (2H; t), 3.67 (2H; s), 4.30 (2H; t), 6.84 (1H; d), 7.10–7.30 (4H; m), 8.02 (1H; m) ppm. MS m/z 367 (MH$^+$). Anal. (C$_{21}$H$_{26}$N$_4$S.2HCl.¾H$_2$O) C, H, N.

EXAMPLE 11

N-[[2-[2-(Diethylamino)ethyl]-2H-[1]-benzothiopyrano[4,3,2-cd]indazol-5-yl ]methyl]methanesulfonamide To a solution of methanesulfonyl chloride (0.172 g, 1.50 mmol) in $CH_2Cl_2$ (30 mL) is added the freebase of the compound of example 8 (0.51 g, 1.28 mmol)) and pyridine (0.4 mL) with stirring at 0° C. After the mixture is allowed to warm to ambient temperature over 5h $CHCl_3$ (30 mL) and 2N NaOH (5 mL) is added to the mixture. The organic layers are separated, washed with water, dried over $Na_2SO_4$, and concentrated in vacuo to give the crude product. Purification by chromatography with 0.5% $Et_3N$ in $CH_2Cl_2$ gives 0.650 g of gum. Recrystallization from ether-methanol (90:10) gives the compound (0.460 g, 84%), mp: 120°–125° C. $^1H$ NMR ($CDCl_3$) 0.98 (6H; t), 2.58 (4H; q), 2.84 (3H; s), 2.92 (2H; t), 4.26 (2H; d), 4.38 (2H; t), 4.48 (1H; b), 6.90 (1H; d), 7.08–7.30 (4H; m), 8.06 (1H; m)ppm. MS m/z 431 ($MH^+$). Anal. ($C_{21}H_{26}N_4O_2S_2.½H_2O$) C, H, N.

EXAMPLE 12

N-[[2-[(2-(Diethylamino)ethyl]-9-methoxyl-2H-[1]-benzothiopyrano[4,3,2-cd]indazol-5-yl]methyl]-methanesulfonamide This compound is prepared via the same procedure used to synthesize the compound of Example 11. Flash chromatography with hexane, hexane:EtOAc (40:60), EtOAc, gives the compound as a gum, (0.785 g, 66%). Recrystallization from ether and a few drops of $CH_2Cl_2$ provides the analytical sample, mp: 125°–126° C. $^1H$ NMR ($CDCl_3$) 0.98 (6H; t), 2.58 (4H; q), 2.84 (3H; s), 2.90 (2H; t), 3.88 (3H; s), 4.26 (2H; d), 4.72 (1H; t), 6.80–6.92 (2H; m), 7.20 (1H; d), 7.22 (1H; d), 7.60 (1H; d) ppm. MS m/z 461 ($MH^+$). Anal. ($C_{22}H_{28}N_4O_3S_2$) C, H, N.

EXAMPLE 13

Methyl N-[[2-[(2-diethylamino)ethyl]-2H-[1]-benzothiopyrano-(4,3,2-cd) indazol-5-yl]methyl) carbamate To a solution of the free base of the compound of Example 8 (0.974 g, 2.45 mmol) in $CH_2Cl_2$ is added methyl chloroformate (0.23 mL) and $Et_3^N$ (0.8 mL) with stirring at 0° C. The mixture is stirred for 5 h and allowed to warm to room temperature. The reaction mixture is diluted with $CHCl_3$ (0.23 mL) and water (15 mL) and basified to pH 10 by adding a few drops of 10% NaOH solution. The organic layers are separated, washed with water, dried over $Na_2SO_4$, and concentrated in vacuo to give crude compound. Purification by chromatography with 0.5% isopropylamine in EtOAc gives 0.62 g of pure material (55%) , mp: 130°–132° C. $^1H$ NMR ($CDCl_3$) 0.98 (6H; t), 2.56 (4H; q), 2.90 (2H; t), 3.66 (2H; s), 4.30 (4H; t,s), 4.98 (1H; b), 6.86 (1H; d), 7.08–7.30 (4H; m), 8.04 (1H; m) ppm. MS m/z 411 ($MH^+$) Anal. Calcd. for $C_{22}H_{26}N_4O_2S$: C, H, N.

EXAMPLE 14

Methyl N-[[2-[(2-(diethylamino)ethyl]-9-methoxy-2H-[1]-benzothiopyrano[4,3,2-cd]indazol-5-yl]methylcarbamate This compound is prepared via the same procedure used to synthesize the crude compound of Example 13. The crude product is flash chromatographed (5% MeOH/EtOAc) to afford pure compound (1.10 g, 63%) as a pale yellow solid, mp 125°–127° C. MS m/z $^1H$ NMR ($CDCl_3$) d 0.98 (6H; t), 2,59 (4H; q), 2.95 (2H; t), 3.70 (3H; s), 4.89 (3H; s), 4.35 (4H; m), 7.15 (2H; m), 7.22 (2H; d), 7.60 (1H; d)

EXAMPLE 15

N-[[2-[(2-(Diethylamino)ethyl]-9-hydroxy-2H-[1]-benzothiopyrano-(4,3,2-cd)-indazol-5-yl]methyl]-methanesulfonamide A solution of the compound of Example 12 (1.02 g, 2.22 mmol) in $CH_2Cl_2$ (50 mL) is cooled to −50° C. and treated dropwise with $BBr_3$ (15 mL of 1M solution in $CH_2Cl_2$, 15 mmol) forming a thick orange suspension. The mixture is allowed to warm to −10° C. and stirred for an additional 2h. The reaction is diluted with $CH_2Cl_2$ (100 mL) and quenched with MeOH (10 mL). The resulting mixture is poured into ice water, neutralized with aqueous NaOH, and extracted with 10%MeOH/$CHCl_3$ (5x) The organic phase is separated and the aqueous phase is washed with brine, dried over $Na_2SO_4$ and concentrated in vacuo to afford a yellow solid (0.87 g) . Dry flash chromatography eluting with EtOAc, then 1% MeoH/EtOAc and finally 1% MeOH/0.2% IPA/ EtOAc elutes the pure product as a white solid (0.44 g, 45%), mp 215°–218° C. (dec.) $^1H$ NMR (DMSO-$d_6$) 0.80 (t, J=7.1 Hz, 6H), 2.44 (q, J=7.1 Hz, 4H), 2.82 (t, J=6.3 Hz, 2H), 2.86 (s, 3H), 4.02 (d, J=6.0 Hz, 1H), 4.33 (t, J=6.1 Hz, 2H), 6.74 (dd, J=2.7, 8.7 Hz, 1H), 7.16 (d, J=8.6 Hz, 1H), 7.26 (d, J=8.3 Hz, 2H), 7.37 (d, J=2.6 Hz, 1H), 7.44 (t, J=6.0 Hz, 1H) 9.78 (s, 1H) .MS m/z 447($MH^+$) Anal. ($C_{21}H_{26}N_4O_3S_2.¼H_2O$) C, H, N.

EXAMPLE 16

Methyl N-[[2-[(2-(diethylamino)ethyl]-9-hydroxy-2H-[1]-benzothiopyrano[4,3,2-cd]indazol-5-yl]-methyl]carbamate This compound is prepared via the same procedure used to synthesize the compound of Example 12. The crude product is purified by dry flash chromatography eluting with EtOAc then 2% MeOH/EtOAc and finally with 1.8% MeOH/0.2% IPA/EtOAc to elute the product. Concentration in vacuo afforded the compound as an off white solid (0.42 g, 61%), mp 239°–240° C. (dec.) $^1H$ NMR ($CDCl_3$) 0.98 (t, J=7.2 Hz, 6H), 2.54 (4, J=7.1 Hz, 4H), 2.86 (t, J=7.2 Hz, 2H), 3.65 (s, 3H), 4.25 (m, 2H), 5.15 (br s, 1H), 6.76 (dd, J=7.2, 8.5 Hz, 1H), 6.85 (d, J=8.6 Hz, 1H), 7.45 (d, J=8.6 Hz, 1H), 7.23 (m, 1H), 7.43 (d, J=2.9 Hz, 1H)ppm. Anal. ($C_{22}H_{26}N_4O_3S$) C,H,N.

EXAMPLE 17

N-[[2-[(2-(Diethylamino)ethyl]-9-methoxy-2H-[1]-benzothiopyrano[4,3,2-cd]indazol-5-yl]methyl]-2-chloroacetamide A solution of the compound of Example 2 (0.73 g, 2.05 mmol) in glacial HOAc (4 mL) at 0° C. is treated with concentrated $H_2SO_4$ and stirred for 15 min. N-hydroxymethylchloroacetamide (0.26 g, 2.10 mmol) is added and the reaction is stirred at ambient temperature for 24 h. The mixture is poured into ice, baseified with 3N NaOH and extracted with CHCl3 (3×50 mL). The organic portion is separated, dried over $Na_2SO_4$ and concentrated in vacuo to afford the crude product. Flash chromatography (silica gel, Hexanes/EtOAc 1:1) afforded pure compound (0.64 g, 70%), mp 167°–169° C. $^1$H NMR (CDCl$_3$) 0.92 (t, 6H), 2.48 (q, 4H), 2.84 (t, 2H), 3.78 (s, 3H), 4.04 (s, 2H), 4.22 (t, 2H), 4.30 (d, 2H), 6.64–6.74 (m, 2H), 6.92 (t, 1H), 7.02 (m, 2H), 7.42 (d, 1H)ppm. MS m/z 462 (MH$^+$). Anal. (C$_{23}$H$_{27}$ClN$_4$O$_2$S) C, H, N.

Representative examples of the invention were tested for antitumor activity.

The test methods were as follows and the results are contained in Table 1.

In Vitro Cytotoxicity

This is measured by quantifying clonogenic survival in soft agar following a 1 hour transient exposure of P388 mouse leukemia cells to drug. The IC$_{50}$ value is the concentration of drug which reduced clonogenic survival by 50%.

Topoisomerase II Inhibition

The promotion by the test compound of covalent complex formation between [$^{32}$P]-end labeled pBR322 DNA and extensively purified HeLa cell topo II is determined by the SDS/K$^+$ precipitation method of Trask, et al., *The EMBO Journal*, 1984, 3, 671–676. EC$_{50}$ values are calculated to be the concentration of the test compound at which the amount of DNA precipitated is equivalent to 50% of the maximum precipitated by m-AMSA in a concomitant control experiment.

DNA Intercalation

A known ethidium bromide displacement assay is used to determine intercalation potency. (Cain, et al., *J. Med. Chem.*, 1978, 21, 658–668.) The EC$_{50}$ value (average of two determinations) is the concentration of test compound necessary to displace 50% of calf thymus DNA bound ethidium bromide.

Murine Antitumor Activaty Versus Pancreatic Ductal Adenocarcinoma #03.

This is done according to the methods of Corbett, et al., *Cytotoxic Anticancer Drugs: Models and Concepts for Drug Discovery and Development*, Kluwer Academic Publishers, Boston, 1992, pp. 35–87; Corbett, et al., *Cancer Res.*, 1984, 44, 717–726.; and LoRusso, et al., *Cancer Res.*, 1990, 50, 4900–4905.

T/C Value

This is tumor growth inhibition, where T is the medium tumor burden in the treatment group times 100 at evaluation and C is the medium tumor burden in the control group at evaluation. A T/C value <42% is considered significant antitumor activity.

MTD

This is the maximum tolerated total dose administered intravenously in mg/kg.

LTC

This means the long term cures, the number of mice in the treatment group with no palpable tumor evidents after a minimum of 86 days/total number in treatment group.

LCK

This means log$_{10}$ cell kill of tumor bearing mice (cures excluded), a calculation based on tumor growth delay; cures for this tumor require >4.5 log kill.

| Compound | in vitro cytox IC50-µM | topo II inhib EC$_{50}$-µM | intercalation EC$_{50}$-µM | murine antitumor activity versus Panc 03 | | | |
|---|---|---|---|---|---|---|---|
| | | | | % T/C | MTD | LTC | LCK |
| Ex 5 | 0.33 | >260 | 1.5 | 0 | 81 | 0/5 | 2.4 |
| Ex 6 | 55 | >240 | 1.9 | 0 | 231 | 3/5 | 3.6 |
| Ex 8 | 5.8 | >250 | 0.12 | 25$^j$ | 72 | 0/5 | m |
| Ex 9 | 13 | >260 | 0.13 | 0$^j$ | 240 | 3/4 | >4.5 |
| Ex 11 | 0.5 | >230 | 1.8 | 0 | 72 | 0/5 | 2.31 |
| Ex 12 | 30 | >210 | 1.6 | 0 | 208 | 3/5 | 2.2 |
| Ex 15 | 0.0044 | 0.55$^k$ | 2.4 | 0$^j$ | 31 | 0/5 | 2.0 |
| Ex 13 | 0.50 | >240 | 2.6 | 0 | 78 | 3/5 | 2.5 |
| Ex 14 | 45 | >220 | 0.79 | 0$^j$ | 170 | 4/4 | >4.5 |
| Ex 16 | 0.011 | 0.33k | 1.5 | 13$^j$ | 18 | 0/5 | m |
| Ex 10 | 16 | >220 | 0.18 | 0 | 326 | 1/5 | 3.6 |
| WIN33377* | 0.301 | 3.0$^k$ | 18 | 0 | 124 | 3/5 | 2.0 |
| mAMSA | 0.151 | 0.72 | 11 | 0 | 48 | 0/5 | 1.5 |

*N-[[1-[[2-(Diethylamino)ethyl]amino]-9-oxothioxanthen-4-yl]methyl]N-methylmethanesulfonamide
$^j$first dose of compound administered 4 days after tumor implantation
$^k$Bell-shaped dose response curve was noted when determining the EC$_{50}$.
m - Not calculated The pharmaceutical compositions of the present invention include one or more of the compounds of this invention formulated into compositions together with one or more non-toxic physiologically acceptable carriers, adjuvants or vehicles which are collectively referred to herein as carriers, for parenteral injection, for oral administration in solid or liquid form, for rectal or topical administration, and the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

The percentage of active component in the composition and method for treating tumors or cancer can be varied so that a suitable dosage is obtained. The dosage administered to a particular patient is variable depending upon the clinician's judgement using as the criteria: the route of administration, the duration of treatment, the size and condition of the patient, the potency of the active component, and the patient's response thereto. An effective dosage amount of active component can thus readily be determined by the clinician considering all criteria and utilizing his best judgement on the patient's behalf.

We claim:
1. A compound of formula

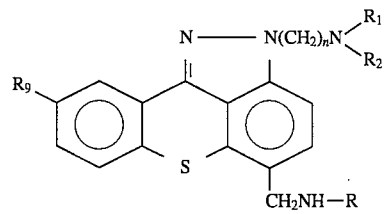

wherein n is 2 or 3;
R is hydrogen, lower-alkyl, C(O)H, C(O)$R_3$, SO$_2$$R_3$, and C(O)OR$_3$;
$R_1$ and $R_2$ are independently hydrogen or lower-alkyl;
$R_3$ is lower-alkyl; and
$R_9$ is hydrogen, lower-alkyl, lower-alkoxy, or hydroxy; or a pharmaceutically acceptable acid-addition salt or solvate thereof.

2. The compound of claim 1, wherein n is 2.
3. The compound of claim 1, wherein $R_1$ and $R_2$ are each ethyl.
4. The compound of claim 1, wherein $R_9$ is hydroxy.
5. The compound of claim 1, wherein R is SO$_2$$R_3$, and C(O)OR$_3$ and $R_3$ is methyl.
6. The compound of claim 1 wherein n is 2; $R_1$ is ethyl, $R_2$ is ethyl and $R_9$ is hydroxy.
7. The compound of claim 1 being
 a) N-[[2-[(2-(Diethylamino)ethyl]-2H-[1]-benzothiopyrano[4,3,2-cd]indazol-5-yl]methyl]formamide;
 b) N-[[2-[(2-(Diethylamino)ethyl]-9-methoxy-2H-[1]-benzothiopyrano[4,3,2-cd]indazol-5-yl]methyl]formamide;
 c) N-[[2-[(2-(Diethylamino)ethyl]-2H-[1]-benzothiopyrano[4,3,2-cd]indazol-5-yl]methyl]-N'-methylformamide;
 d) 2-[(2-(Diethylamino)ethyl]-2H-[1]-benzothiopyrano[4,3,2-cd]indazole-5-methanamine;
 e) 2-[(2-(Diethylamino)ethyl]-9-methoxy-2H-[1]-benzothiopyrano[4,3,2-cd]indazole-5-methanamine;
 f) N-methyl-2-[(2-(Diethylamino)ethyl]-2H-[1]-benzothiopyrano[4,3,2-cd]indazole-5-methanamine;
 g) N-[[2-[2-(Diethylamino)ethyl]-2H-[1]-benzothiopyrano[4,3,2-cd]indazol-5-yl]methyl]methanesulfonamide;
 h) N-[[2-[(2-(Diethylamino)ethyl]-9-methoxyl-2H-[1]-benzothiopyrano[4,3,2-cd]indazol-5-yl]methyl]methanesulfonamide;
 i) Methyl N-[[2-[(2-diethylamino)ethyl]-2H-[1]-benzothiopyrano( 4,3,2-cd) indazol-5-yl]methyl)carbamate;
 j) Methyl N-[[2-[(2-(diethylamino)ethyl]-9-methoxy-2H-[1]-benzothiopyrano[4,3,2-cd]indazol-5-yl]methylcarbamate;
 k) N-[[2-[(2-(Diethylamino)ethyl]-9-hydroxy-2H-[1]-benzothiopyrano-( 4,3,2-cd)-indazol-5-yl]methyl]methanesulfonamide;
 l) Methyl N-[[2-[(2-(diethylamino)ethyl]-9-hydroxy-2H-[1]-benzothiopyrano[4,3,2-cd]indazol-5-yl]methyl] carbamate; or
 m) N-[[2-[(2-(Diethylamino)ethyl]-9-methoxy-2H-[1]-benzothiopyrano[4,3,2-cd]indazol-5-yl]methyl]-2-chloroacetamide.

8. A pharmaceutical composition which comprises a compound of claim 1 and a pharmaceutically acceptable carrier or diluent.

9. A pharmaceutical composition which comprises a compound of claim 6 and a pharmaceutically acceptable carrier or diluent.

10. A pharmaceutical composition which comprises a compound of claim 7 and a pharmaceutically acceptable carrier or diluent.

11. A method for treating a tumor in a mammal which comprises administering to said mammal an amount of a compound of claim 1 effective to reduce the size of said tumor.

12. A method for treating a tumor in a mammal which comprises administering to said mammal an amount of a compound of claim 6 effective to reduce the size of said tumor.

13. A method for treating a tumor in a mammal which comprises administering to said mammal an amount of a compound of claim 7 effective to reduce the size of said tumor.

* * * * *